United States Patent [19]

Neuhaus

[11] Patent Number: 5,101,674
[45] Date of Patent: Apr. 7, 1992

[54] METHOD AND A DEVICE FOR A CONTACTLESS POSITIONING OF A LIQUID SAMPLE

[75] Inventor: Dietmar Neuhaus, Duesseldorf, Fed. Rep. of Germany

[73] Assignee: Deutsche Forschungsanstalt fur Luft- und Raumfahrt e.V., Cologne, Fed. Rep. of Germany

[21] Appl. No.: 518,211

[22] Filed: May 3, 1990

[30] Foreign Application Priority Data

May 4, 1989 [DE] Fed. Rep. of Germany ....... 3914711

[51] Int. Cl.$^5$ .......................................... G01N 37/00
[52] U.S. Cl. ......................... 73/864.91; 156/DIG. 62
[58] Field of Search ...................... 73/864.91, 863, 37; 156/DIG. 62, 600, 620.74; 432/58

[56] References Cited

U.S. PATENT DOCUMENTS

B 431,785  2/1976  Nagorsen .................. 156/DIG. 62

Primary Examiner—Jerry W. Myracle
Attorney, Agent, or Firm—Spensley Horn Jubas & Lubitz

[57] ABSTRACT

For positioning a liquid sample which is held together by surface tension to form a drop, a plurality of lances is provided that are directed onto the sample from different spatial directions. Sintered bodies are provided on the lances, from which gas escapes. The escaping gas prevents a contact between the sintered bodies and the sample. The lances are positioned so close to the sample that indentations are formed in the latter.

8 Claims, 2 Drawing Sheets

METHOD AND A DEVICE FOR A CONTACTLESS POSITIONING OF A LIQUID SAMPLE

BACKGROUND OF THE INVENTION

1. Field of the Invention

The present invention relates to a method and a device for a contactless positioning of a liquid sample.

2. Description of Related Art

In various testing and production methods, it is necessary to position a drop of liquid contactlessly, e.g. when examining the phase transition from the liquid phase to the solid phase, or when examining phenomena of crystallization. Known contactless positioning methods use electromagnetic or ultrasonic fields to keep the sample in a defined spatial position. Positioning a liquid by means of electromagnetic fields is restricted to electrically conductive liquids. Accoustic positioning devices cause a mixing of the liquid which is not always desired. Moreover, in accordance with gas-film technology, it is known to keep liquids in a hovering state in a crucible permeable to gas. However, it is difficult to observe the liquid through the walls of the crucible.

It is an object of the present invention to provide a method and a device for a contactless positioning of a liquid sample in order to keep the sample in its position with simple means and without the use of electromagnetic or ultrasonic fields.

SUMMARY OF THE INVENTION

According to the present invention, the liquid is held in position by lance-shaped devices. Each individual lance consists of a tube, the end of which carries a body permeable to gas. This gas-permeable body forms the tip of the lance. It is slightly introduced into the liquid, so that the liquid sample is indented by the tip of the lance without, however, getting into contact with the tip of the lance. A contact is prevented by a gas film emanating from the tip of the lance. A plurality of such lances is arranged around the liquid, thus defining the space determined for the liquid. The closer the lances are arranged, the greater are the holding forces that position the liquid by making use of the surface tension. It is particularly advantageous to select the arrangement of the lances such that the lance tips imitate the shape that the liquid surface takes due to the action of the surface tension alone and without any interference from outside.

The lances acting on the liquid from different sides leave enough free space at the surface of the liquid to observe the liquid or to further influence the liquid, e.g. by heating with heat radiation.

The device of the present invention is particularly suited for positioning a liquid sample (melt) in a speculum metal furnace. In this case, not only the liquid, but also the solidified melt is held in position by the lances. Without any difficulties, a change in volume of the sample is possible without ceasing the positioning.

The method and the device are particularly suited for an implementation under conditions of zero-gravity or reduced gravity, e.g. in spacecrafts. In these cases, the positioning forces that must act on the sample in order to maintain the same in a defined position, are extremely low.

In order to position a sample in all three spatial directions, at least four lances should preferably be used. Under zero-gravity conditions, the lances should preferably be spatially distributed at equal distances around the sample. In this state, the lance tips are located at the corners of a tetrahedron. If a larger number of lances is used, the tips will preferably be situated at the corners of an octahedron, hexahedron, icosahedron etc.

BRIEF DESCRIPTION OF THE DRAWINGS

The following is a detailed description of an embodiment of the present invention with reference to the accompanying drawings.

In the Figures

DESCRIPTION OF THE PREFERRED EMBODIMENT

Figure 1:
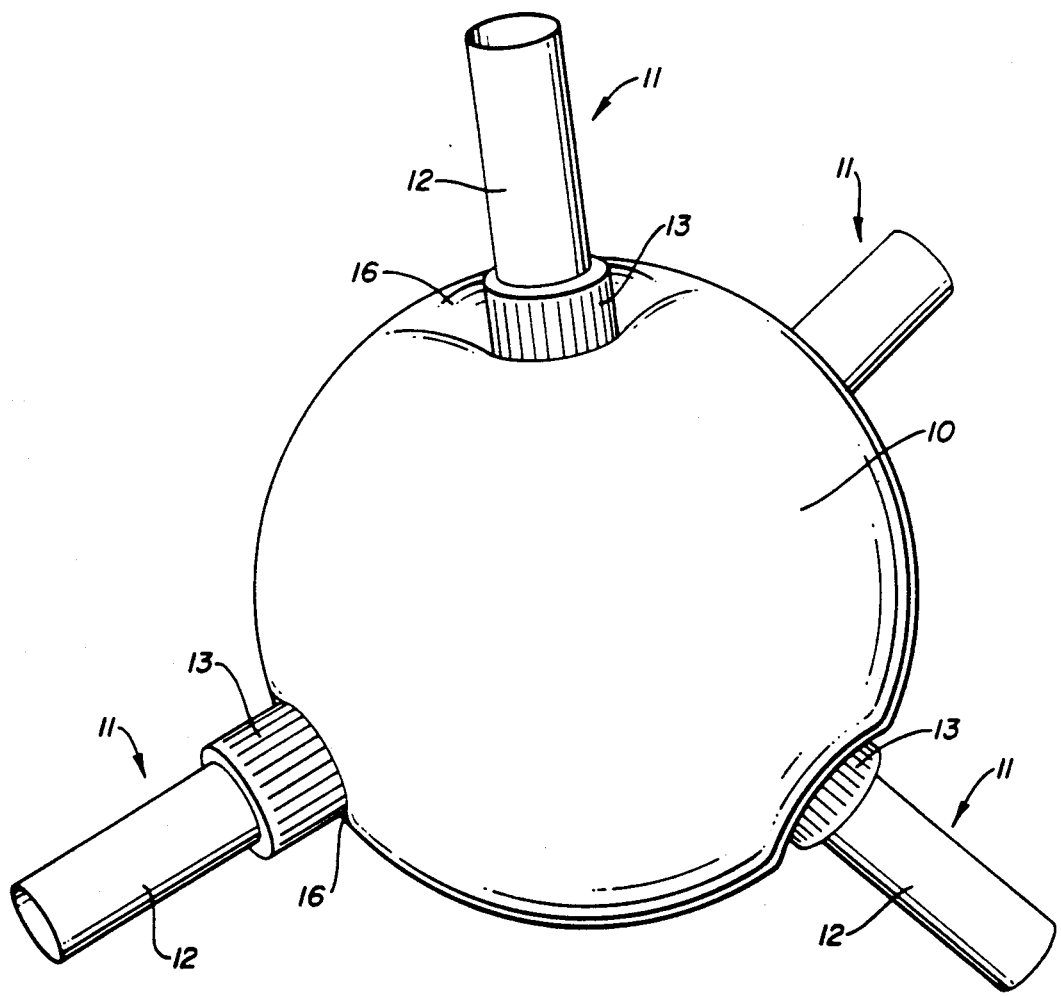
FIG. 1 is a perspective illustration of a sample held inbetween four lances.
Figure 2:
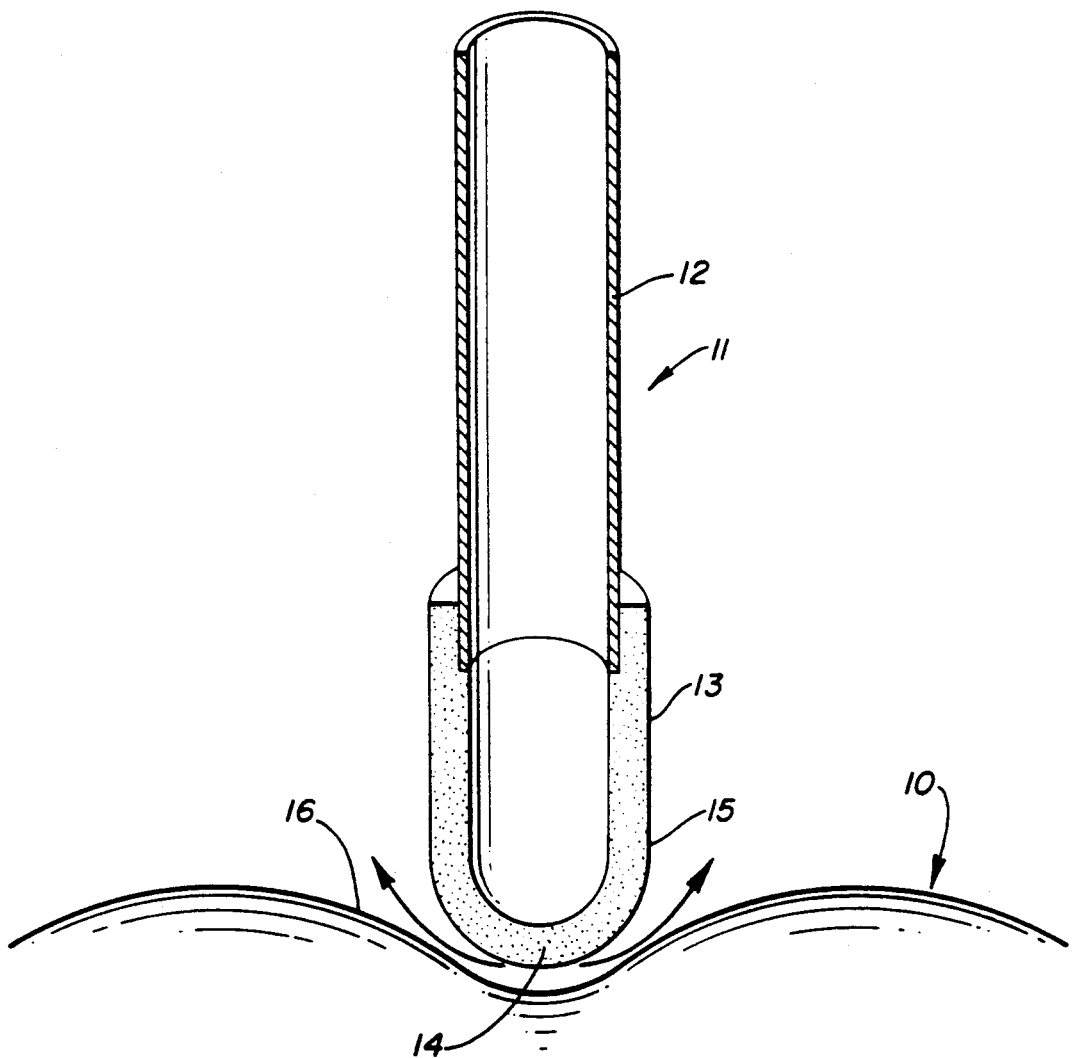
FIG. 2 is a cross section of one of the lances.

FIG. 1 illustrates a liquid sample 10, e.g. a melt of metal, under zero-gravity conditions. In this case, the liquid sample is spherical in shape, provided there are no external influences, the surface tension acting to maintain the spherical shape.

From different spatial directions, a total of four lances 11 acts on the drop of liquid, which are orientated such that their axes point toward the center of the space holding the sample and intersect in the center of the same. Each lance 11 consists of a tube 12 connected to a gas supply and has its front end provided with a crest-shaped porous body 13. This body 13 has an arched front face 14 and consists of sintered material or a fine web of wire. From the wall of the body 13, gas emanates uniformly distributed so that no sharp jet of gas is formed. The outer surface of the body 13 forms the gas outlet surface 15.

The lances 11 extend so close to the center point of the positioning center of the sample 10 that the crest-shaped bodies 13 cause indentations 16 in the sample 10. The gas flow emanating from the gas outlet surface 15 forms a gas pad around the body 13 that presses against the indentation 16 in a positioning manner and prevents a contact between the sample 10 and the body 13.

In a correct positioning, the indentations caused on the sample 10 by all the lances 11 have the same depth. Should the sample be shifted from this set position, at least one indentation 16 will become deeper than before, and a restoration of the set position is caused by the surface tension of the sample 10 which tends to make all identations 16 have the same depth.

I claim:

1. A device for contactlessly positioning a liquid sample, the device comprising force applying means including at least four lances directed onto said sample from different spatial directions, each of the lances having an end provided with a gas outlet surface, characterized in that said gas outlet surface is provided at a crest-shaped porous body.

2. The device according to claim 1, characterized in that said porous body is a sintered body.

3. The device according to claim 1, characterized in that said porous body is a web of wires.

4. A device as in claim 1 wherein the liquid sample is in reduced gravity space.

5. A device as in claim 1 wherein the liquid sample is in zero gravity space.

6. A device for contactlessly positioning a liquid sample, comprising:

force applying means including at least four lances, each of the lances having an end provided with a gas outlet surface, the lances being arranged about the sample so that the gas outlet surface of each lance is directed toward the sample from a different direction, whereby gas escaping from the gas outlet surfaces of the lances positions the sample and prevents contact between the lances and the sample, wherein the gas outlet surface of each lance comprises a crest-shaped porous body.

7. The device according to claim 6, wherein the porous body comprises a sintered body.

8. The device according to claim 6, wherein the porous body comprises a web of wires.

* * * * *